US012751843B2

(12) United States Patent
Al-Saadon

(10) Patent No.: US 12,751,843 B2
(45) Date of Patent: Oct. 6, 2026

(54) BIFURCATED DUAL-BALLOON CATHETER SYSTEM FOR BIFURCATED VESSELS

(71) Applicant: Khalid Al-Saadon, Sarnia (CA)

(72) Inventor: Khalid Al-Saadon, Sarnia (CA)

( * ) Notice: Subject to any disclaimer, the term of this patent is extended or adjusted under 35 U.S.C. 154(b) by 651 days.

(21) Appl. No.: 17/517,755

(22) Filed: Nov. 3, 2021

(65) Prior Publication Data

US 2022/0054287 A1 Feb. 24, 2022

Related U.S. Application Data

(62) Division of application No. 14/422,559, filed as application No. PCT/CA2013/000163 on Feb. 25, 2013, now abandoned.

(30) Foreign Application Priority Data

Aug. 20, 2012 (WO) ................ PCT/CA2012/000771

(51) Int. Cl.
*A61F 2/856* (2013.01)
*A61F 2/82* (2013.01)
(Continued)

(52) U.S. Cl.
CPC ................ *A61F 2/856* (2013.01); *A61F 2/82* (2013.01); *A61F 2/954* (2013.01); *A61F 2/958* (2013.01);
(Continued)

(58) Field of Classification Search
CPC .. A61F 2/852; A61F 2/856; A61F 2/86; A61F 2/82; A61F 2/954; A61F 2/958;
(Continued)

(56) References Cited

U.S. PATENT DOCUMENTS 4,994,071 A 2/1991 Macgregor
5,669,924 A * 9/1997 Shaknovich ............ A61F 2/958 606/198

(Continued)

FOREIGN PATENT DOCUMENTS

EP 897700 A1 2/1999
JP 11057019 A 3/1999

(Continued)

OTHER PUBLICATIONS

EP Search Report for Application No./Patent No. 13830477.9 1651 / 2884949 PCT/CA2013/000163 dated Mar. 29, 2016 (8 pages).

(Continued)

*Primary Examiner* — Christopher D. Prone
(74) *Attorney, Agent, or Firm* — Barnes & Thornburg LLP

(57) ABSTRACT

A bifurcated dual-balloon catheter apparatus for deploying one or more stents to a bifurcated vessel or for use in angioplasty procedures involving bifurcated vessels. The apparatus is particularly suited for bifurcated vessels of the type having a main branch from which a side branch extends therefrom. The apparatus has a main branch balloon and a side branch balloon. A conduit is provided in the main branch balloon through which a portion of the side branch balloon extends. The first balloon is positionable within the main branch of the vessel while the distal portion of the second balloon is positionable within the side branch such that when the first and second balloons are inflated, the first balloon expands radially in the main branch while the distal portion of said second balloon maintains registration with the side branch by expanding radially therein.

16 Claims, 4 Drawing Sheets

(51) Int. Cl.

| | |
|---|---|
| ***A61F 2/954*** | (2013.01) |
| ***A61F 2/958*** | (2013.01) |
| ***A61M 25/01*** | (2006.01) |
| ***A61M 25/09*** | (2006.01) |
| ***A61M 25/10*** | (2013.01) |
| ***B29C 49/08*** | (2006.01) |
| *B29L 31/00* | (2006.01) |

(52) U.S. Cl.
CPC ........ *A61M 25/09* (2013.01); *A61M 25/1011* (2013.01); *A61M 25/1029* (2013.01); *A61M 25/104* (2013.01); *B29C 49/08* (2013.01); *A61M 2025/0183* (2013.01); *A61M 2025/1045* (2013.01); *B29L 2031/7543* (2013.01)

(58) Field of Classification Search
CPC A61M 25/09; A61M 25/1011; A61M 25/104; A61M 2025/0183; A61M 2025/1045
See application file for complete search history.

(56) References Cited

U.S. PATENT DOCUMENTS

| | | | | |
|---|---|---|---|---|
| 5,749,825 | A * | 5/1998 | Fischell .................. | A61F 2/958 600/3 |
| 6,017,324 | A | 1/2000 | Tu et al. | |
| 6,033,435 | A | 3/2000 | Penn et al. | |
| 6,056,775 | A | 5/2000 | Borghi et al. | |
| 6,096,073 | A * | 8/2000 | Webster .................. | A61F 2/915 623/1.16 |
| 6,165,195 | A * | 12/2000 | Wilson .................... | A61F 2/958 606/108 |
| 6,210,429 | B1 | 4/2001 | Vardi et al. | |
| 6,325,826 | B1 * | 12/2001 | Vardi ...................... | A61F 2/915 623/1.35 |
| 6,346,089 | B1 | 2/2002 | Dibie | |
| 6,695,877 | B2 | 2/2004 | Brucker et al. | |
| 6,740,113 | B2 | 5/2004 | Vrba | |
| 7,438,721 | B2 | 10/2008 | Doig et al. | |
| 7,481,834 | B2 | 1/2009 | Kaplan et al. | |
| 9,486,342 | B2 | 11/2016 | Al-Saadon | |
| 10,463,518 | B2 | 11/2019 | Al-Saadon | |
| 2002/0177866 | A1 * | 11/2002 | Weikel ............... | A61B 17/7258 606/192 |
| 2006/0030924 | A1 | 2/2006 | Van Der Leest et al. | |
| 2006/0100694 | A1 | 5/2006 | Globerman | |
| 2007/0016241 | A1 | 1/2007 | Von Oepen et al. | |
| 2007/0208406 | A1 | 9/2007 | Alkhatib et al. | |
| 2008/0033521 | A1 | 2/2008 | Jorgensen et al. | |
| 2008/0125847 | A1 | 5/2008 | Krever et al. | |
| 2008/0171975 | A1 | 7/2008 | Jennings et al. | |
| 2008/0208307 | A1 | 8/2008 | Ben-Muvhar et al. | |
| 2009/0171430 | A1 | 7/2009 | Baim et al. | |
| 2009/0287148 | A1 | 11/2009 | Martin et al. | |
| 2009/0292241 | A1 | 11/2009 | Von Oepen et al. | |
| 2011/0307047 | A1 | 12/2011 | Bourang et al. | |
| 2012/0089220 | A1 | 4/2012 | Lualdi | |
| 2014/0214147 | A1 | 7/2014 | Al-Saadon | |
| 2017/0007431 | A1 | 1/2017 | Al-Saadon | |

FOREIGN PATENT DOCUMENTS

| | | | |
|---|---|---|---|
| JP | 2007510491 | A | 4/2007 |
| WO | 9634580 | A1 | 5/1996 |
| WO | 9741803 | A1 | 11/1997 |
| WO | 0139697 | A1 | 6/2001 |
| WO | 03074118 | A1 | 9/2003 |
| WO | 2006033126 | A1 | 3/2006 |
| WO | 2013026135 | A1 | 2/2013 |

OTHER PUBLICATIONS

PCT Search Report and Written Opinion for PCT/CA/2013/000163, completed Apr. 19, 2013.
English translation of the Office Action for JP Patent Application No. 2015-527741 dated Nov. 29, 2016 (5 pages).
European Search Report from related EP 12 82 5596, dated Feb. 27, 2015 (8 pages).
Chinese Search Report for Application No. 201380044178.X dated Jan. 4, 2016 (7 pages).
Communication pursuant to Article 94(3) EPC for EP Patent Application No. 13 830 477.9 1651 dated Nov. 22, 2016 (5 pages).
Notification of the Second Office Action issued in corresponding Chinese Patent Application No. 201380044178.X dated Aug. 22, 2016 (in Chinese with English translation) (13 pages).

* cited by examiner

BIFURCATED DUAL-BALLOON CATHETER SYSTEM FOR BIFURCATED VESSELS

CROSS-REFERENCE TO RELATED APPLICATIONS

This application is a divisional of U.S. application Ser. No. 14/422,559, filed Feb. 19, 2015, which is a national stage entry under 35 USC § 371(b) of PCT International Application Serial No. PCT/CA2013/000163 filed Feb. 25, 2013, which claims priority to PCT International Application Serial No. PCT/CA2012/000771 filed Aug. 20, 2012, each of which is hereby incorporated by reference herein.

FIELD OF THE INVENTION

The present invention relates to an inflatable balloon apparatus for deploying one or more stents to a bifurcated vessel or for use in angioplasty procedures involving bifurcated vessels. The apparatus is particularly suited for bifurcated vessels of the type comprising a main branch from which a side branch extends therefrom.

BACKGROUND OF THE INVENTION

The term stent has been used interchangeably with terms such as intraluminal vascular graft and expansible prosthesis. As used throughout this specification, the term stent is intended to have a broad meaning and encompasses any expandable prosthetic device for implantation in a body passageway (e.g. a lumen or artery).

There have been various attempts at addressing the delivery and deployment of stents at bifurcated lesions. Bifurcated vessels may be of the Y-type, wherein a main branch bifurcates into two secondary branches, or of the T-type, wherein a side branch extends from a main branch. While the subject invention may be employed in certain circumstances with Y-type bifurcated vessels, it is primarily directed for use with T-type bifurcated vessels. The term "vessel" as used herein generally means a tubular tissue within the cardiac, coronary, renal, peripheral vascular, gastrointestinal, pulmonary, urinary and neurovascular systems and brain.

Applicant's prior patent application PCT/CA2012/000771 filed Aug. 20, 2012, and incorporated herein by reference, discloses a unique stent system and deployment system therefor particularly suited for use with bifurcated vessels of the type having a main branch from which a side branch extends therefrom. That stent system generally comprises a first radially expandable stent for supporting the walls of the main branch and a second radially expandable stent for supporting the walls of the side branch. The second stent has a shaped proximal end adapted to engage a complementary-shaped opening in the side wall of the first stent during expansion. The second stent can also include alignment means or brace for orienting its proximal end with the opening of the first stent. The first and second stents may intersect at a relative angle of between about 10° and 170° and in this regard, the shape of the opening of the first stent and the shaped end of the second stent may be based on the geometries of intersecting cylinders. The length and diameter of the stents may be selected based on the predetermined shapes of the main and side branches.

Other previous balloon delivery systems that assist in positioning the stents with accuracy in the bifurcated lesions, particularly involved in the procedure of double balloon sequential dilation for the stent, have not proven to be very successful. Their limitations have led to the development of specifically designed balloons to treat bifurcation lesions, such as in U.S. Pat. No. 6,017,324 to Tu et al. This design has its limitations in that it will help to solve specific bifurcation lesions when the distal branches have a Y-shape and the size of the distal vessels are smaller than the size of the proximal vessel (e.g. the aortic artery at bifurcation with iliac arteries) but it is not suitable if the size of one of the distal branches is equal to the proximal vessel size, and not suitable for the side branched vessels which are the majority of the cases.

Applicant's aforementioned patent application PCT/CA2012/000771 discloses several embodiments of inflatable balloon apparatuses suited for delivery of one or more stents to a bifurcated vessel, and more particularly suited to the deployment of the aforementioned bifurcated stent system. In general, the inflatable deployment apparatuses described therein comprise a main branch portion, with proximal and distal ends, and a side branch portion that originates from a mid-region the side of the main branch portion, preferably about mid-distance between the proximal and distal ends, and extends outwardly therefrom, preferable at an angle of between about 10 and 170° relative to the main branch portion. The inflatable portions are either unitary and contiguous, or may comprise dual balloons which are connectable to a common or separate supply of gas or fluid for inflation. The difficulty in using two balloons at a T-shaped bifurcated vessel is that the balloons overlap in one side of the main branch. When expanded, this causes the overlapping balloon portions to expand more than the distal portion of the balloon in the other side of the main branch, resulting in uneven circumferential expansion of the stent in the main branch. To overcome this problem, a restrictive member, such as a sleeve, is positioned around the portions of the balloons which overlap. The sleeve restricts the expansion of the proximal ends of the balloons to about the same extent as the expansion of the distal end of the first balloon. In this manner, the main stent may be expanded uniformly in the main branch as the first and second balloons are expanded. The sleeve also assists in keeping the balloons in better parallel position during deployment. To provide additional support where the side branch portion extends from sleeve, a support band may be provided to prevent the sleeve from tearing upon inflation of the balloons. While the balloons could be of uniform tubular shape, with the same or differing diameters, to help reduce any over-expansion of the proximal ends of the balloons within the sleeve and, hence, over-stretching of the vessel walls during expansion, the main branch portion may include a longitudinal groove that extends along its proximal end portion to about the midpoint or a point between its proximal end and distal end where the distal end of the second balloon is adapted to extend. The proximal end portion of the side branch balloon is accommodatable at least in part within the groove. To help ease the stress at the bending point of the side branch balloon, it may be formed with an angular bend. The resulting reduction in stress at the bending point lessens the propensity of tearing of the sleeve during inflation. The side branch balloon can also be made with its proximal and distal ends being of differing diameters on either side of the bend. A reverse bend may also be provided which allows the distal end of the side branch balloon to remain substantially parallel to the main branch balloon for ease of insertion.

One of the drawbacks of Applicant's prior dual balloon designs, is that the use of restrictive sleeves and/or additional support bands, or the side-by-side overlapping of the proximal portions of the balloon, even with the provision of the grooved main branch balloon, increases the effective wall thickness and/or bulk of the balloon system at certain locations. This can lead to inconsistent inflation as well as a lessening of flexibility of the balloon catheter system during deployment. A disadvantage with respect to the use of a contiguous or unitary balloon system is that the size of the catheter usually needs to be of a larger diameter to accommodate the three lumens for receiving the guide wires for the main branch balloon portion and the side branch balloon portion as well as for the communication of inflation fluid. However, with a dual balloon system, separate catheters having included lumen pairs for guide wires and inflation fluids may be used which actually has been found to reduce the overall diameter needed therefor. This reduction in the catheter bulk leads to further reduction of the overall profile of the dual balloon catheter system and increased flexibility.

There is, therefor, a need to reduce the overall effective wall thickness at the location where the balloons tend to overlap, i.e., their proximal end portion. It would be advantageous if a system (arrangement) could be derived which could eliminate the need for a sleeve or other restrictive member, and therewith its additional bulk, while still maintaining the consistent minimal profile. It would be further advantageous to be able to restrict the expansion of the proximal end portions without necessitating the use of an additional restrictive sleeve or support band. Elimination of the sleeve would result in the following advantages:

1) Less bulky balloon profile, which will make it easier to advance the system in small or tortuous vessels;
2) Better crimping of the stent(s) over a lower profile bifurcated balloon; and
3) Reduce inconsistent inflation of the sleeved and non-sleeved sections of the balloons.

SUMMARY OF THE INVENTION

The present invention solves the aforementioned and other disadvantages of the prior art by providing a dual-balloon bifurcated balloon catheter for use in angioplasty or as a delivery system for placement of one or more stents in the main vessel and/or the branched vessel of a bifurcated vessel with high accuracy.

In general, one of object of the present invention to provide a bifurcated dual-balloon catheter for performing balloon dilatation procedures in body lumens, such as those shown and described in Applicant's aforementioned patent application PCT/CA2012/000771. Another object of the present invention to provide a highly flexible, low-profile bifurcated dual-balloon catheter for use in angioplasty procedures or for positioning of one or more stents in bifurcated vessels. It is a further object of the invention to provide a bifurcated dual-balloon catheter system which in inflatable in a predetermined and consistent manner. It is yet another object of the invention to provide a bifurcated dual-balloon catheter system which reduces or eliminates side-by-side overlapping of the balloons.

These and other objects of the invention are realized by the invention described herein. In particular, there is provided in accordance with one aspect of the invention:

an inflatable apparatus for use in a bifurcated vessel having a main branch from which a side branch extends therefrom, comprising:

a first balloon and a second balloon each having proximal and distal ends and proximal and distal portions;

a conduit extending longitudinally through the first balloon from a first opening proximate the proximal end of the first balloon to a second opening disposed between the proximal and distal ends of the first balloon;

said second balloon being arranged such that its proximal portion is accommodated within the conduit and its distal portion extends through the second opening;

the first balloon being positionable within the main branch of the vessel while the distal portion of the second balloon is positionable within the side branch such that when the first and second balloons are inflated, the first balloon expands radially in the main branch while the distal portion of said second balloon maintains registration with the side branch by expanding radially therein.

Preferably, the balloons of the invention are made using a stretch blow moulding (aka "molding") process. In order to provide for the conduit using this process, there is provided in another aspect of this invention, a double split mould (aka "mold") comprising split lower and upper halves. The upper half is further split into lower half halves across a section which includes a mandrel for forming the conduit so as to also split the mandrel. A formed main branch conduited balloon can be removed from the double split mould by separating the lower and upper mould halves and the lower half halves.

By providing the main branch balloon with an internal conduit adapted to accommodate the proximal end portion of the side branch balloon, the profile of the balloon system can be significantly minimized and the need for an additional restrictive member or other support band for keeping the proximal portions of the balloons together is eliminated, further minimizing the profile of the balloon system.

The inflatable "balloon" portions referred to herein are generally included within two broad classes. One class is considered non-compliant, and are formed from a generally non-stretchable material such as polyethylene, polyethylene terephthalate, polypropylene, cross-liked polyethylene, polyamide, and the like. The other class is considered compliant, formed from a generally compliant or stretchable material such as nylon, silicon, latex, polyurethane and the like.

The apparatus may be used in angioplasty procedures, Alternately, the apparatus may also be used as a double-stent apparatus and a single-stent apparatus, each of which may be used to cover the origin of the bifurcation in a branched vessel. As a single-stent apparatus, the invention may be used to treat only one branch of the bifurcation while leaving access to the second branch unobstructed. The invention may be used to provide different sizes and lengths of the branched balloon delivery system and different sizes and lengths of the stents needed to be delivered in the bifurcated lesions.

The balloon apparatus of the present invention is imageable by methods commonly used during catheterization such as by x-ray through the use of fluorescent inflation fluid and fluorescent markers on the balloon catheters.

These objects and other object advantages and features of the invention will become better understood from the detailed description of the invention and the accompanying drawings.

DETAILED DESCRIPTION OF THE INVENTION

Figure 1:
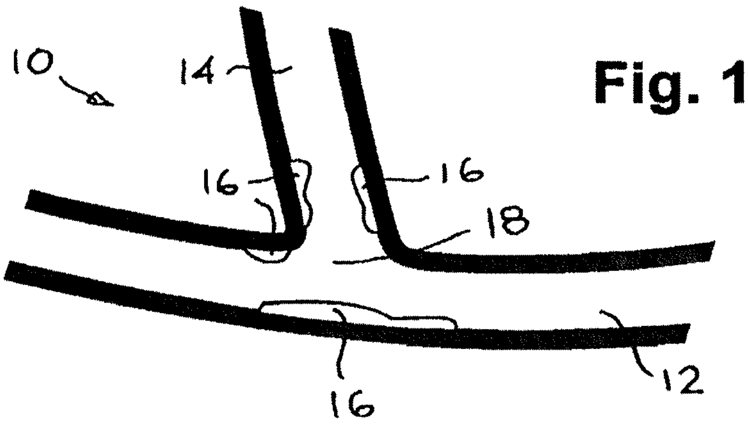
FIG. 1 is a schematic representation of a bifurcated vessel and in particular a side branched bifurcated vessel.

FIG. 1 shows a typical bifurcated vessel 10 of the T-type comprising a main vessel 12 and a side branch vessel 14 extending therefrom and having plaque or lesions 16 at or about the juncture 18 of the vessels 12, 14.

Figure 2A:
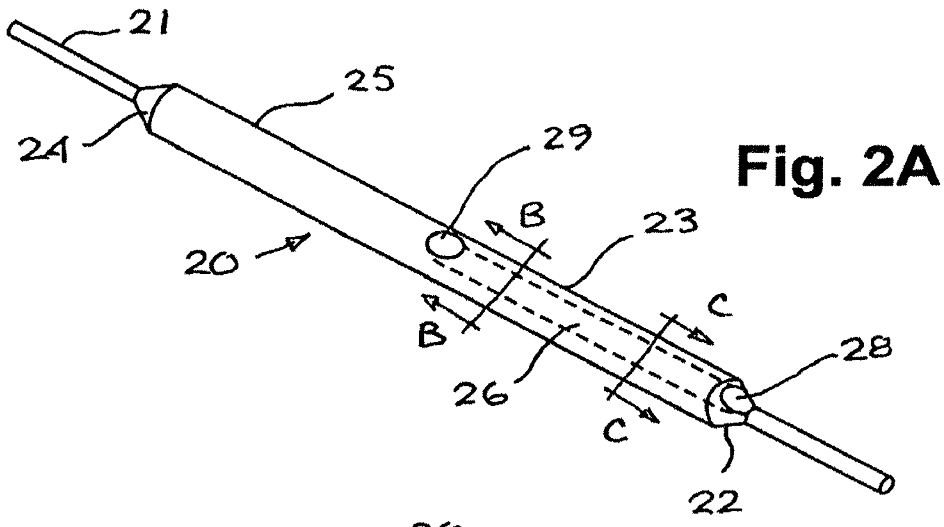
FIG. 2A is a perspective view illustrating the first or main branch balloon of the dual balloon deployment apparatus.

The preferred embodiment of the first or main branch balloon is illustrated at 20 in FIG. 2A in its expanded state. The main branch balloon 20 is disposed on a portion of a catheter 21 which extends through the main branch balloon 20. Catheter 21 is used to deploy the balloon 20 to the bifurcated vessel region through the use of guide wires (not shown in FIG. 2A) as well as to communicate inflation fluid to the balloon 20. The portion of the catheter 21 within the balloon 20 is not shown (with hidden lines) for sake of clarity. Similarly, the catheter 21 may contain one or more lumens, which are also not shown for sake of clarity. Main branch balloon 20 has a proximal end 22 and a distal end 24. When the terms proximal and distal are used herein, they normally imply relativity to the insertion of the catheter. Main branch balloon 20 is of a generally uniform tubular shape having a predetermined inflatable diameter which approximates the diameter of the main branch of the vessel in which the dual-balloon deployment apparatus is to be deployed.

A longitudinal internal conduit 26 is provided within main branch balloon 20 that extends through a portion of the balloon 20. The internal conduit 26 has an entry opening 28 at or near the immediate proximal end 22 of the main branch balloon 20 and an exit opening 29 at about the midpoint or a point between the proximal end 22 and distal end 24 where the distal end of the second balloon (not shown in FIG. 2) is adapted to extend. The location of the exit opening 29 generally separates the main branch balloon 20 into a proximal half or proximal portion 23 and a distal half or distal portion 25.

Figure 2B:
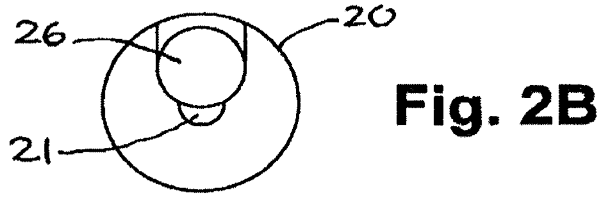
FIGS. 2B and 2C are enlarged cross-sectional views taken along lines B-B and C-C of FIG. 2A showing the internal details of the proximal portion of the first or main branch balloon of the dual balloon deployment apparatus.
Figure 2C:
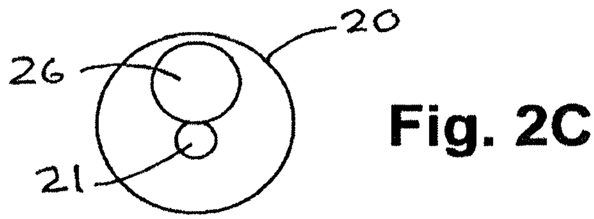

FIGS. 2B and 2C show the main branch balloon 20 in enlarged cross-sections taken along lines B-B and C-C of FIG. 2A, respectively. The cross-sections show the conduit 26 as well as the catheter 21 from both directions. For clarity purposes, the lumens, if provided, are not shown in the cross-section.

Figure 3:
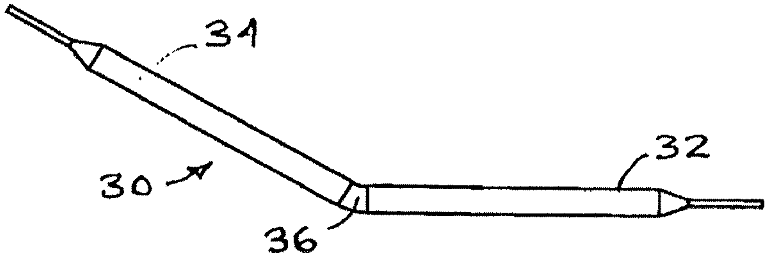
FIGS. 3 to 5 are side views illustrating various embodiments of the second balloon of a dual balloon deployment apparatus suitable for use with the first or main branch balloon of the present invention.
Figure 4:
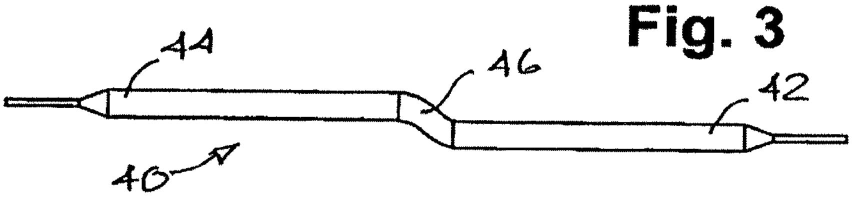
Figure 5:
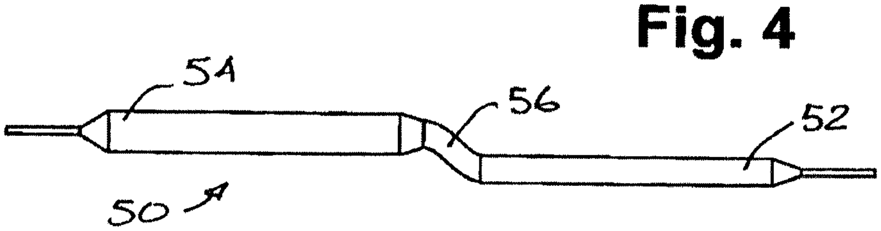

Various possible embodiments of the second or side branch balloon are shown in FIGS. 3 to 5 which embodiments are similar to those shown and described at FIGS. 25 to 27 of Applicant's aforementioned patent application No. PCT/CA2012/000771. FIG. 3 shows a second balloon 30 as having a uniform tubular shape with substantially equal-sized proximal 32 and distal 34 portions. To help ease the stress at the bending point, the second balloon 30 may be formed with an angular bend 36, between the proximal 32 and distal 34 portions. The reduction in stress may also lessen the propensity of tearing of the sleeve during inflation. In FIG. 4, there is shown at 40 an alternate embodiment of the second balloon, wherein a reverse bend 46 is provided between the proximal 42 and distal 44 portions. The reverse bend 46 allows the distal end 44 of the second balloon 40 to remain substantially parallel to the first balloon (not shown) for ease of insertion during deployment.

Another modification in the shape of the side branch second balloon is shown at 50 in FIG. 5. In this preferred embodiment, the second balloon 50 is provided with a proximal portion 52 which is of reduced diameter relative to the diameter of the distal portion 54. The proximal portion 52 and the distal portion 54 are separated by a reverse bend 56. The advantage of reducing the diameter size of the proximal portion 52 of the side branch second balloon 50 is that it will allow for better accommodation within the conduit 26 of the main branch balloon 20 as will be shown and described below with respect to FIGS. 6A and 6B.

Figure 6A:
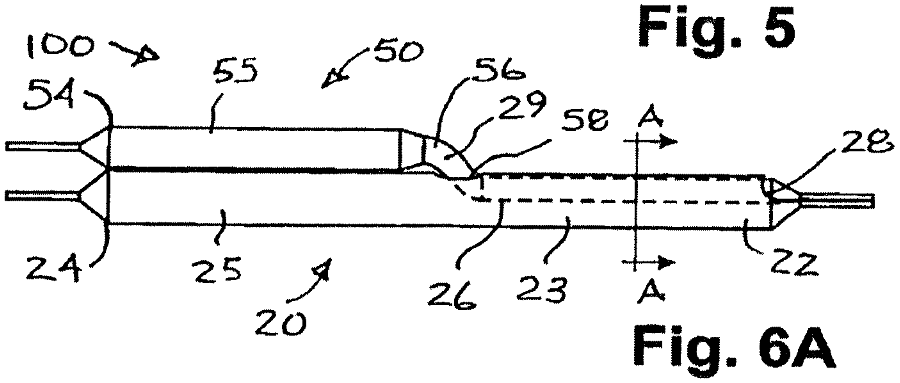
FIG. 6A is a side view of preferred embodiment of the dual balloon deployment apparatus.
Figure 6B:
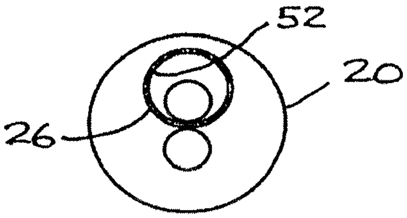
FIG. 6B is an enlarged cross-sectional showing the details of the proximal portion of the preferred dual balloon deployment apparatus.

In FIG. 6A, there is shown a preferred embodiment of a dual balloon deployment apparatus 100 comprising the conduited first balloon embodiment 20 as shown in FIG. 2A with the second balloon embodiment 50 as shown in FIG. 5. The reduced diameter proximal portion 52 of the second balloon 50 is positioned within conduit 26 in the proximal portion 22 of the first balloon 20, as can be seen in cross-section in FIG. 6B, with the distal portion 54 of the side branch balloon 50 exiting at the reverse bend 56 through exit opening 29.

It will be understood that inflation of the main branch balloon 20 will result in pressure being exerted radially inwardly on the conduit 26, but contraction of the conduit will be substantially counteracted by the inflation of the proximal portion 52 of the second or side branch balloon 50 when the second or side branch balloon 50 is inflated and at steady state. The conduit 26 thus acts as a restricting means (in lieu of a sleeve) which limits the expansion of the proximal portion 52 of the side branch balloon 50 during its inflation and which will, therefor, substantially prevent inconsistent inflation or over-inflation of the proximal portion 22 of the main branch balloon 20 relative to the distal portion 24 during co-inflation.

The proximal portions 22,52 of the first and second balloons 20,50 and the distal portion 24 of the first balloon 20 forms a primary inflatable portion for expanding a main branch stent (not shown) in the main vessel 12 (see FIG. 1) while the distal end portion 54 of the second balloon 50 maintains registration with the associated side branch vessel 14 when deploying only a main branch stent, or may subsequently or contemporaneously be used to expand a side branch stent (not shown) into the side branch vessel 14. Without the stents the device is similarly functional for angioplasty procedures at the bifurcated vessel 10.

The shapes of the first balloon 20 and of the distal portion 54 of said second balloon (i.e. length and inflatable diameter) may be selected based on the predetermined shapes and/or characteristics of the main and side branches 12, 14, respectively. The shape of the proximal portion 52 of the second balloon 50 is selected based on the shape of the conduit 26 and so as to minimize stresses to the extent possible when both first and second balloons 20, 50 are inflated.

Figure 7:
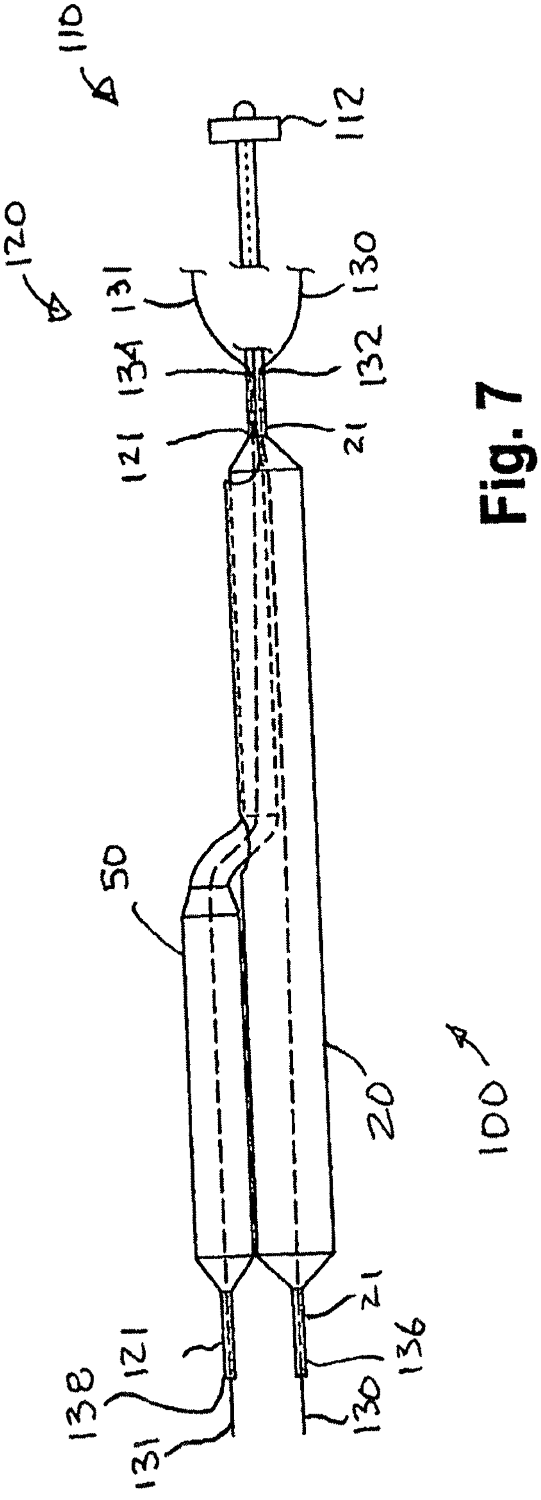
FIG. 7 is an enlarged side view illustrating the dual balloon deployment apparatus with its catheter and wire systems.

FIG. 7 shows an enlarged view of the preferred embodiment of the dual balloon stent deployment apparatus 100 including a preferred inflation system 110 and wire guidance system 120. As previously described, the main branch balloon has a main branch catheter 21 which goes through its entire length. Similarly, the side branch balloon 50 has a side branch catheter 121 which extends through its entire length. The portions of the catheters 21, 121 within the balloons 20, 50 are not shown (with hidden lines) for sake of clarity, but they will be understood to exist. A main branch guide wire 130 is disposed within the catheter 21 of which enters the catheter 21 on its proximal side at proximal entry point 132 and exits the catheter 21 through its distal end 136. Similarly, a side branch guide wire is disposed within the catheter 121 which enters the catheter 121 on its proximal side at proximal entry point 134 and exits the catheter 121 through its distal end 138. These guide wires 130,131 are, as shown, preferably of the rapid exchange system type. However, over the wire exchange systems could also be used. Separate lumens (not shown) may be provided within catheters 21,121 through which the guide wires 130,131 extend.

Catheters 21,121 also provide the means by which the interior of the inflatable balloons communicate with the supply of gas or fluid for inflation through valve 112, shown schematically. The supply can be a single source or separate sources may be provided, which can be controlled unitarily or separately. Lumens (not shown) may also be used within catheters 21,121 for the communication of the inflation gas or liquid from the supply.

Figure 8A:
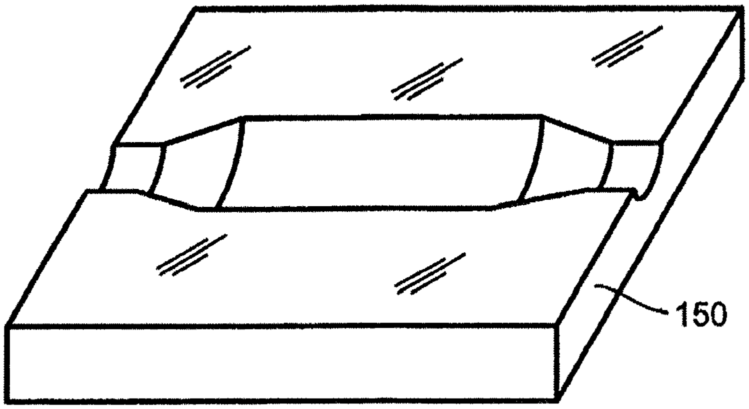
FIGS. 8A and 8B are perspective views of the mould components used in the production of the main branch balloon of the present invention.
Figure 8B:
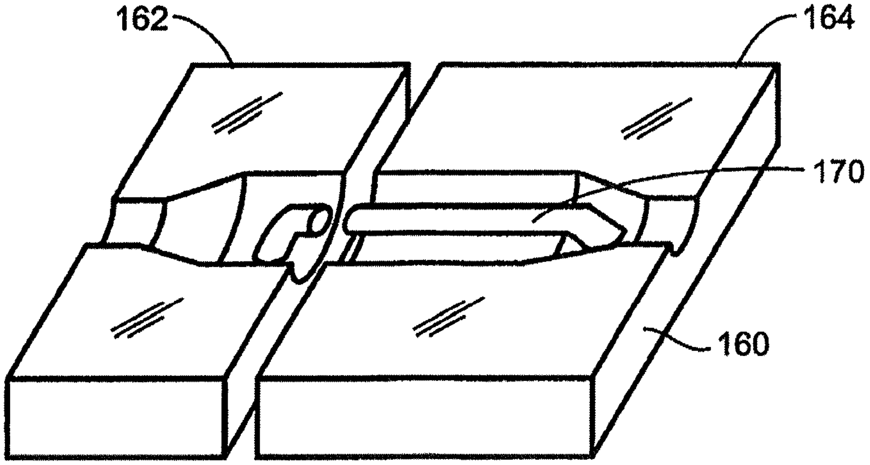

The balloons of this invention are preferably made through a stretch blow moulding process in which polymer-based tubing is stretched under pressure and at elevated temperature in a biaxial fashion both longitudinally and radially. Finally, the formed balloon is cooled using chilled circulating water while maintaining a high internal pressure to set the dimension and shape of the balloon. The provision of the conduit 26 in the main branch balloon 50 presents challenges using this process which were solved by providing a double-split mould as shown in FIGS. 8A and 8B. The mould is first split between a lower mould half 150 and an upper mould half 160. In order to form the conduit 26, a mandrel 170 is provided. However, in order to be able to be able to remove the formed balloon from the mould halves 150,160, the upper mould half 160, including the mandrel 170, is also split as shown in FIG. 8B. Thus, this provision of a double-split mould allows the main branch balloon 50 to be formed with a through conduit 26.

Although there have been shown various embodiments and examples of the inflatable deployment apparatus, it will be appreciated by those skilled in the art that these embodiments and examples should not be considered limiting and that various modifications and substitutions may be made to the inventions defined in the appended claims without departing from the spirit and scope of the invention.

The invention claimed is:

1. An inflatable apparatus for use in a bifurcated vessel having a main branch from which a side branch extends at an angle therefrom, comprising:

a first balloon and a second balloon each having proximal and distal ends and proximal and distal portions;

a conduit extending longitudinally through said first balloon from a first opening proximate the distal end of said first balloon to a second opening disposed between said proximal and distal ends of said first balloon;

said second balloon being arranged such that its proximal portion is disposed within said conduit and its distal portion extends through the second opening;

said first balloon being positionable within said main branch while the distal portion of said second balloon is positionable within said side branch such that when said first and second balloons are inflated with the proximal portion of the second balloon remaining within the conduit of the first balloon during inflation of the second balloon, said first balloon expands radially in said main branch while the distal portion of said second balloon maintains registration with said side branch by expanding radially therein, wherein the second balloon includes a pre-formed bend section located where the distal portion of the second balloon extends through the second opening of said first balloon, and wherein said bend section comprises an S-shaped bend adapted to enable the distal portion of said second balloon to remain substantially parallel to the first balloon during insertion, and to conform to the angle of the side branch during inflation.

2. The apparatus of claim 1 wherein said second opening is located approximately midway between the proximal and distal ends of said first balloon.

3. The apparatus of claim 1 wherein the shape of the first balloon and the shape of the distal portion of said second balloon are selected based on predetermined shapes of the main and side branches, respectively.

4. The apparatus of claim 1, wherein said first and second balloons are inflatable concurrently.

5. The apparatus of claim 1, wherein said first and second balloons are inflatable separately.

6. The apparatus of claim 1 further comprising a catheter extending through each of said first and second balloons.

7. The apparatus of claim 6, wherein said catheters each accommodate a guide wire system for use in the positioning of the main branch balloon in the main branch of the vessel and the distal portion of the side branch balloon in the side branch of the vessel.

8. The apparatus of claim 7, wherein said guide wire system for positioning of the main branch balloon is a rapid exchange wire system.

9. The apparatus of claim 7, wherein said side wire system for positioning of the side branch balloon is a rapid exchange wire system.

10. The apparatus of claim 1, further comprising a first radially-expandable stent positioned on said first balloon, wherein when said first balloon is inflated, said first stent radially expands within said main branch.

11. The apparatus of claim 10, wherein said first radially-expandable stent comprises a side opening through which the distal end of said second balloon extends.

12. The apparatus of claim 11, further comprising a second radially-expandable stent positionable on the distal end of said second balloon, wherein when said second balloon is inflated, said second stent radially expands within said side branch.

13. The apparatus of claim 12, wherein said second stent has a proximal and distal end and said proximal end is shaped to cooperate with said opening of said first stent upon expansion.

14. The apparatus of claim 1, wherein the second balloon portion is extendable at an angle of between 10° and 170° from said first balloon when said balloons are inflated.

15. The apparatus of claim 1, wherein the main and side branch balloon are made using a stretch blow molding process.

16. The apparatus of claim 15, wherein the main branch balloon is made in a double split mold comprising a lower half and an upper half, said upper half being further split into lower half halves across a section which includes a mandrel for forming said conduit so as to also split said mandrel, whereby a formed main branch conduited balloon can be removed from said double split mold by separating the lower and upper mold halves and the lower half halves.

* * * * *